US012578348B2

(12) United States Patent
Banack et al.

(10) Patent No.: US 12,578,348 B2
(45) Date of Patent: Mar. 17, 2026

(54) BLOOD INDICATORS OF ALZHEIMER'S DISEASE

(71) Applicant: The Institute for Ethnomedicine, Jackson, WY (US)

(72) Inventors: Sandra Anne Banack, Jackson, WY (US); Paul Alan Cox, Jackson, WY (US)

(73) Assignee: THE INSTITUTE FOR ETHNOMEDICINE, Jackson, WY (US)

( * ) Notice: Subject to any disclaimer, the term of this patent is extended or adjusted under 35 U.S.C. 154(b) by 548 days.

(21) Appl. No.: 17/665,057

(22) Filed: Feb. 4, 2022

(65) Prior Publication Data

US 2022/0252620 A1 Aug. 11, 2022

Related U.S. Application Data

(60) Provisional application No. 63/146,031, filed on Feb. 5, 2021.

(51) Int. Cl.
*G01N 33/68* (2006.01)

(52) U.S. Cl.
CPC ..... *G01N 33/6896* (2013.01); *G01N 33/6812* (2013.01); *G01N 2800/2821* (2013.01)

(58) Field of Classification Search
CPC ........... G01N 33/6812; G01N 33/6896; G01N 2800/2821; G01N 2800/50
See application file for complete search history.

(56) References Cited

U.S. PATENT DOCUMENTS

| | | | |
|---|---|---|---|
| 10,578,629 B2 | 3/2020 | Federoff et al. | |
| 2008/0161228 A1 | 7/2008 | Ryals et al. | |
| 2012/0237510 A1 | 9/2012 | Spee et al. | |
| 2013/0156846 A1 | 6/2013 | Rodgers et al. | |
| 2014/0357525 A1 | 12/2014 | Kaddurah-Daouk et al. | |
| 2018/0275144 A1 | 9/2018 | Cohen et al. | |
| 2019/0137516 A1 | 5/2019 | Ikeuchi et al. | |
| 2020/0332301 A1 | 10/2020 | Turano et al. | |

FOREIGN PATENT DOCUMENTS

WO 2020/203878 A1 10/2020

OTHER PUBLICATIONS

Kling, Mitchel A., et al. "Circulating ethanolamine plasmalogen indices in Alzheimer's disease: Relation to diagnosis, cognition, and CSF tau." Alzheimer's & Dementia 16.9 (2020): with Supplemental Information, 30 pages. (Year: 2020).*
Graham, Stewart F., et al. "1 H NMR metabolomics investigation of an Alzheimer's disease (AD) mouse model pinpoints important biochemical disturbances in brain and plasma." Metabolomics 9 (2013): with Supplemental Information, 14 pages (Year: 2013).*
Tsolaki, M. et al. "Monotherapy with Lamotrigine in patients with Alzheimer's disease and seizure", 2000, American Journal of Alzheimer's Disease, 15(2), 74-79 (Year: 2000).*
Ellison DW et al. Phosphoethanolamine and ethanolamine are decreased in Alzheimer's disease and Huntington's disease. Brain Res. 1987, 417(2):389-392; abstract only. (Year: 1987).*
Seki Y et al. Cerebrospinal fluid taurine after traumatic brain injury. Neurochem Res. 2005, 30(1):123-128. (Year: 2005).*
Patent Cooperation Treaty, International Search Report issued in PCT/IB2022/051010, Apr. 28, 2022, pp. 1-2.
Csernansky et al., "CSF excitatory amino acids and severity of illness in Alzheimer's disease", Neurology, Jun. 1, 1996, pp. 1715-1720, vol. 46(6).
Ellison et al., "Phosphoethanolamine and ethanolamine are decreased in Alzheimer's disease and Huntington's disease", Brain Research, Aug. 11, 1987, pp. 389-392, vol. 417(2), Abstract.
European Patent Office, Extended European Search Report issued in EP Patent Application No. 22749344.2, Nov. 25, 2024, pp. 1-8.
Kim et al., "Small molecule biomarkers in Alzheimer's disease", Oilseeds & Fats Crops and Lipids, 2018, pp. 1-22, vol. 25(4).
Japanese Intellectual Property Office, Official Action Issued in Japanese Patent Application No. 2023-547403, Nov. 11, 2025, pp. 1-2. English Translation.

* cited by examiner

*Primary Examiner* — Kimberly Ballard

(74) *Attorney, Agent, or Firm* — Pillsbury Winthrop Shaw Pittman LLP

(57) ABSTRACT

Presented herein are methods of identifying a subject who has, or is at risk of developing Alzheimer's disease comprising determining a presence or amount of 2-aminoethyl dihydrogen phosphate or taurine in the blood, or a blood product, obtained from the subject. Also presented herein are methods of preventing, treating or delaying the onset of Alzheimer's disease.

21 Claims, 2 Drawing Sheets

BLOOD INDICATORS OF ALZHEIMER'S DISEASE

CROSS-REFERENCE TO RELATED APPLICATIONS

This application claims the benefit and priority from U.S. Provisional Patent Application No. 63/146,031 filed Feb. 5, 2021, titled "BLOOD INDICATORS OF ALZHEIMER'S DISEASE", the contents of which are incorporated herein by reference in their entirety.

FIELD OF THE INVENTION

Certain embodiments of the invention relate to methods of detecting the presence, absence or amount of 2-aminoethyl dihydrogen phosphate and/or taurine in a sample. Certain embodiments of the invention also relate to amounts of 2-aminoethyl dihydrogen phosphate and/or taurine, or ratios of 2-aminoethyl dihydrogen phosphate to taurine in a sample that are predictive and/or diagnostic of Alzheimer's disease. Certain embodiments of the invention also relate to methods of monitoring the progression of Alzheimer's disease, and/or determining a treatment of Alzheimer's disease.

INTRODUCTION

Ninety-five percent of Alzheimer's disease (AD) cases occur in people over 60-65 years old. This is typically a time in life when individuals are looking forward to their golden years and are poised to make significant contributions to their families and communities. AD robs them not only of life, but prior to death burdens them with inability to form or access short-term memories, increasing confusion, disorientation, social withdrawal, and increasing dementia which intensifies during their last years of life. Neuropathologically, onset of AD symptoms are sometimes correlated with brain neuropathology, particularly amyloid-β-42 (Aβ42) plaques and a dense tauopathy of neurofibrillary tangles (NFTs) composed of hyperphosphorylated tau deposits in specific brain regions.

There is likely a significant latency period between the initiation of AD-type neuropathology in the brain and onset of clinical symptoms. A study using $^{14}$C decay from detonation of the 50 megaton Tsara bomba by the Soviet Union on Oct. 31, 1961, which injected a tremendous amount of $^{14}$C into the atmosphere, allowed precise dating of NFTs and Aβ42 plaques extracted from postmortem brain tissues from AD patients. In two of the six patients studied, the NFTs were dated seven years prior to onset of symptoms and in one patient the Aβ42 plaque dated nine years prior to symptom onset. The advantage of discovering and using biomarkers for AD, particularly during the latency period, could be used to explore new types of treatment or even test previously failed drugs, which could eventually be prescribed at a much earlier period of disease progression.

A recent meta-analysis suggested that several CSF biomarkers resulting from amyloid deposition, neuronal damage and loss, and the formation of NFTs, notably phosphorylated-tau (P-tau), amyloid-beta (Aβ42), total-tau (T-tau), as well as neurofilament light protein (NFL), were strongly associated with AD. Blood plasma concentration of T-tau was also indicated as a potentially good indicator of AD, requiring further research, while plasma concentrations of Aβ40 and Aβ42 did not appear to be good candidates for AD diagnosis. Imaging biomarkers assessing amyloid-beta plaques (PiB-PET scans), tau deposits (tau-PET), brain atrophy (structural MRI), memory-related activity patterns (fMRI), and decreased glucose metabolism (FDG-PET) are also currently in use as AD biomarkers.

SUMMARY

As described herein, blood plasma levels of 2-aminoethyl dihydrogen phosphate (also known as phosphoethanolamine) and/or taurine are not known to be associated with Aβ42, hyperphosphorylated tau, and NFT, and can differentiates blood samples of AD patients from blood samples of controls in replicate studies using independent cohorts. Accordingly, the amounts or ratios of 2-aminoethyl dihydrogen phosphate and/or taurine are useful in predicting AD onset, often in asymptomatic patients. Furthermore, as the amounts of 2-aminoethyl dihydrogen phosphate and taurine are easily measured using instruments common in most large hospitals to assess metabolic diseases, their detection and quantitation may be rapidly implemented in a variety of clinical institutions.

Presented herein, in certain embodiments, are methods of determining amounts of 2-aminoethyl dihydrogen phosphate and/or taurine in a sample. In some embodiments, such methods can be used for the diagnosis and early detection of Alzheimer's disease.

Certain aspects of the technology are described further in the following description, examples, claims and drawings.

DETAILED DESCRIPTION

Figure 1:
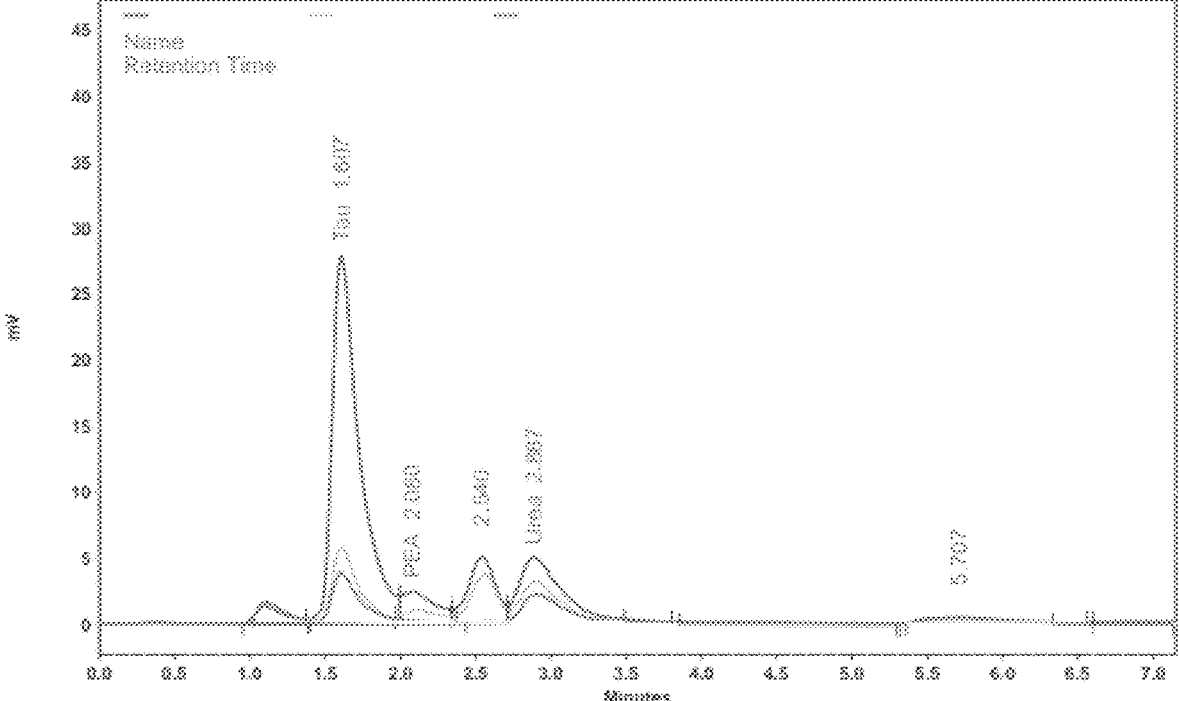
FIG. 1 shows Hitachi amino acid analyzer chromatogram: taurine (Tau, 1.607 min), and phosphoethanolamine (2-aminoethyl dihydrogen phosphate, 2.080 min). The lower-most line shows the absence of 2-aminoethyl dihydrogen phosphate in a control sample; the middle line shows 2-aminoethyl dihydrogen phosphate in an AD sample; and the upper-most line shows a large taurine peak that artificially lifts the 2-aminoethyl dihydrogen phosphate creating a larger area under the curve profile in experiment 2.

As described herein, blood plasma amounts of 2-aminoethyl dihydrogen phosphate and/or taurine have diagnostic and therapeutic utility and provide insight as to whether a subject has, or is at risk of developing, Alzheimer's disease. Accordingly, in some embodiments, methods are provided herein for treatment of asymptomatic subjects who are at risk of developing Alzheimer's disease. Such methods can inhibit the progression of Alzheimer's disease, or delay the onset of Alzheimer's disease.

In some embodiments, an amount of 2-aminoethyl dihydrogen phosphate and/or taurine is determined in a sample. A "sample" is often obtained from a suitable subject using a suitable method. A sample can be isolated or obtained directly from a subject or part thereof. In some embodiments, a sample obtained from a subject is a sample derived from the subject. In certain embodiments, a sample obtained from a subject is obtained from a third party, for example a third party who obtained or extracted the sample from the subject. In some embodiments, a sample is obtained indirectly from an individual or a medical professional. A sample can be any specimen that is isolated or obtained from a subject or part thereof. A sample can be any tissue or fluid that is isolated or obtained from one or more subjects. Non-limiting examples of samples include fluids or tissues obtained or derived from a subject, including, without limitation, blood or a blood product (e.g., serum, plasma, platelets, buffy coats, lymphatic fluid or the like), umbilical cord blood, chorionic villi, amniotic fluid, cerebrospinal fluid (CSF), spinal fluid, lavage fluid (e.g., lung, gastric, peritoneal, ductal, ear, arthroscopic), a biopsy sample, celiocentesis sample, cells (blood cells, lymphocytes, placental cells, stem cells, bone marrow derived cells, embryo or fetal cells, neurons) or parts thereof (e.g., mitochondrial, nucleus, extracts, lysates, or the like), urine, feces, sputum, saliva, nasal mucous, prostate fluid, lavage, semen, lymphatic fluid, bile, tears, sweat, breast milk, breast fluid, and the like or combinations thereof. In some embodiments, a sample comprises or consists of blood or a blood product. In some embodiments, a blood product comprises plasma.

In certain embodiments described herein, a sample is obtained from a subject, a subject is determined to have, or to be at risk of having AD and/or a treatment (e.g., administration of a drug) is administered to a subject. Non-limiting examples of subjects include mammals, humans, non-human primates (e.g., apes, gibbons, chimpanzees, orangutans, monkeys, macaques, and the like), domestic animals (e.g., dogs and cats), farm animals (e.g., horses, cows, goats, sheep, and pigs) and experimental animals (e.g., mouse, rat, rabbit, and guinea pig). In some embodiments, a subject is a mammal. In certain embodiments, a subject is a primate. In some embodiments, a subject is a non-human primate. In some embodiments, a subject is vervet. In certain embodiments, a subject is human. A subject can be any age or at any stage of development, for example, an adult (e.g., 18, 19, 20 or 21 years and older), a senior adult (e.g., over the age of 55, over the age of 60, or over the age of 65 years), a teen (e.g., age 12 to 19 yrs.), child (e.g., age 1 to 12 yrs.), infant (e.g., from birth to 1 yr.), or a mammal in utero. A subject can be male or female.

In some embodiments, a subject has, is suspected of having, or is at risk of developing, Alzheimer's disease. In some embodiments, a subject who has Alzheimer's disease is a subject diagnosed as having Alzheimer's disease by a method described herein. In some embodiments, a subject who has Alzheimer's disease is a subject diagnosed as having Alzheimer's disease by a medical professional (e.g., a medical doctor) based on, for example the presence of one or more diagnostic symptoms and/or the results of one or more standardized diagnostic test results. A subject suspected of having Alzheimer's disease is often a subject not yet diagnosed as having Alzheimer's disease by a medical professional. In some embodiments, a subject suspected of having Alzheimer's disease may display one or more symptoms of Alzheimer's disease, which symptoms are not conclusive evidence that the subject has Alzheimer's disease. In some embodiments, a subject who is suspected of having Alzheimer's disease may have one or more symptoms of Alzheimer's disease, but is not diagnosed as having Alzheimer's disease because there is not enough data to indicate conclusively that the subject has Alzheimer's disease. In some embodiment, a subject who is suspected of having Alzheimer's disease is a subject suspected of having AD, but is not yet diagnosed as having AD by a medical professional.

In some embodiments, a subject is determined to be a subject at risk of developing Alzheimer's disease by conducting a method described herein. In some embodiments, a subject at risk of developing Alzheimer's disease is a subject who is asymptomatic for Alzheimer's disease. In some embodiments, a subject at risk of developing Alzheimer's disease is a subject having one or more symptoms of Alzheimer's disease, which symptoms may be mild or transient in nature. In some embodiments, a subject at risk of developing Alzheimer's disease is a subject who is not yet diagnosed as having Alzheimer's disease. In some embodiments, a subject at risk of developing Alzheimer's disease is a subject suspected of having Alzheimer's disease.

In some embodiments, a subject is a healthy subject. A healthy subject is often a subject that does not have a neurodegenerative disease or disorder. A healthy subject is often a subject that does not have and/or does not display any symptoms of a neurodegenerative disease or disorder. In some embodiments, a healthy subject is a subject that does not have Alzheimer's disease. In some embodiments, a healthy subject is a subject that does not have and/or does not display any symptoms of Alzheimer's disease. In certain embodiments, a healthy subject is a subject between the ages of 18 and 40 years.

In some embodiments a method described herein identifies a subject who has, or is at risk of developing, Alzheimer's disease (AD). In some embodiments a method described herein comprises a method of treating a subject who is determined to have, or to be at risk of developing, AD. In some embodiments, a subject is identified as having, or at risk of having Alzheimer's disease by a method herein, and the method further comprises administering a suitable treatment to the subject (e.g., by administration of a suitable drug).

In some embodiments, a method of treating Alzheimer's disease comprises inhibiting or delaying the onset or progression of Alzheimer's disease. In some embodiments, a method of treating Alzheimer's disease comprises inhibiting or delaying the onset or progression of one or more symptoms of AD. In some embodiments, a method of treating Alzheimer's disease comprises reducing or mitigating one or more symptoms of Alzheimer's disease.

In some embodiments, a method of treating Alzheimer's disease comprises administering a therapeutically effective amount of a suitable Alzheimer's drug to a subject. Non-limiting examples of an AD drug include L-serine, ralitoline, phenytoin, lamotrigine, carbamazepine, lidocaine, tetrodotoxin, nitroindazole, a sulforaphane or sulforaphane analogue, gabapentin, pregabalin, mirogabalin, gabapentin enacarbil, phenibut, imagabalin, atagabalin, 4-methylpregabalin, PD-217,014, riluzole, edaravone, tetrabenazine, haloperidol, risperidone, quetiapine, amantadine, levetiracetam, clonazepam, citalopram, escitalopram, fluoxetine, sertraline, olanzapine, valproate, carbamazepine, lamotrigine, a vaccine (e.g., an immunogenic amount of an amyloid peptide, or a fragment or variant thereof, with or without an adjuvant), a cholinesterase inhibitor (e.g., donepezil, galantamine or rivastigmine), memantine, an antidepressant, an N-methyl D-aspartate (NMDA) antagonist, an omega-3 fatty acid, curcumin or a curcumin derivative, vitamin E, a sleep aid (e.g., zolpidem, eszopiclone or zaleplon), an anti-anxiety drug (e.g., lorazepam or clonazepam), an anti-convulsant (e.g., sodium valproate, carbamazepine, or oxcarbazepine), an anti-psychotic (e.g., risperidone, quetiapine or olanzapine), carbidopa-levodopa, amantadine, a dopamine agonist (e.g., pramipexole, ropinirole, rotigotine or apomorphine), a Monoamine Oxidase Type B (MAO-B) inhibitor (e.g., selegiline, rasagiline or safinamide), a Catechol-O-methyltransferase (COMT) inhibitor (e.g., entacapone or tolcapone), an anticholinergic (e.g., benztropine or trihexyphenidyl), and the like and combinations thereof. In some embodiments, an Alzheimer's drug is selected from one or more of ralitoline, phenytoin, lamotrigine, carbamazepine, lidocaine, tetrodotoxin, riluzole (RILUTEK®; TIGLUTIK®), edaravone (RADICAVA®), gabapentin, pregabalin, mirogabalin, gabapentin enacarbil, phenibut, imagabalin, atagabalin, 4-methylpregabalin, PD-217,014, trihexyphenidyl, amitriptyline, baclofen, diazepam, L-serine, CK-2127107 (reldesemtiv), nusinersen, onasemnogeme abeparovec-xioi (ZOLGENSMA®), NUEDEXTA®, and the like or combinations thereof. In some embodiments, an AD drug comprises L-serine, a salt, metabolic precursor, derivative, polymer or conjugate thereof.

L-Serine

In some embodiments, a subject is administered a therapeutically effective amount of L-serine, a salt, metabolic precursor, derivative or conjugate thereof. In some embodiments, a subject is administered a therapeutically effective amount of free L-serine, or a salt thereof. A therapeutically effective amount of L-serine or free L-serine may be administered as a pharmaceutical composition comprising one or more pharmaceutical excipients, additives, carriers and/or diluents. In some embodiments, a method herein comprises administering a therapeutically effective amount of a composition comprising, consisting of, or consisting essentially of L-serine, a salt, metabolic precursor, derivative or conjugate thereof to a subject. In some embodiments, a method herein comprises administering a therapeutically effective amount of a composition comprising, consisting of, or consisting essentially of free L-serine, or a salt, derivative or conjugate thereof to a subject. In some embodiments, a method herein comprises administering a therapeutically effective amount of a composition comprising, consisting of, or consisting essentially of a polymer of L-serine, or a salt, derivative or conjugate thereof to a subject. In some embodiments, a composition consisting essentially of L-serine, free L-serine, or a salt, a precursor, a derivative or a conjugate thereof excludes proteins or protein fractions comprising less than 100%, 99%, 98%, less than 95%, less than 90%, less than 80%, less than 70%, less than 60%, or less than 50% L-serine (wt/wt). In some embodiments, a composition consisting essentially of L-serine, free L-serine, or a salt, a precursor, a derivative or a conjugate thereof excludes proteins or protein fractions comprising greater than 5%, greater than 10%, greater than 20%, greater than 30%, greater than 40%, greater than 50% or greater than 60% protein (wt/wt). In some embodiments, a composition consisting essentially of L-serine comprises free L-serine, or a polymer of L-serine having an amino acid content of L-serine of at least 99%, 98%, 95%, 90%, 85% or at least 80%. In some embodiments, a composition consisting essentially of L-serine excludes creatine, creatine pyruvate, guanidinoacetic acid (GA), glycocyamine, N-amidinoglycine, and salts or esters thereof. In some embodiments, a composition consisting essentially of L-serine is a composition comprising free L-serine at a purity of at least 85%, at least 90%, at least 95%, at least 98%, at least 99% or 100%. In certain embodiments, a composition consisting essentially of L-serine, free L-serine, or a salt, a precursor, derivative or conjugate of L-serine, is a composition that also comprises zinc.

Free L-serine refers to L-serine in the form of a single amino acid, or a salt thereof. In some embodiments, a composition comprises free L-serine at a purity of at least 85%, at least 90%, at least 95%, at least 98%, at least 99% or 100%. In certain embodiments, free L-serine is not covalently bonded to any other amino acid.

In some embodiments, a composition comprising L-serine may exclude other active ingredients. In some embodiments, a composition may exclude proteins containing L-serine. In some embodiments, a composition may exclude proteins having a molecular weight greater than 10 kDa, greater than 20 kDa, greater than 30 kDa or greater than 50 kDa. In some embodiments, a composition may exclude proteins containing less than 99%, 98%, 95%, 92%, 90%, 80%, 70%, 60%, or less than 50% L-serine. In some embodiments, a composition may exclude creatine, or any energy metabolism precursor of creatine, such as guanidino-acetic acid (GA), equivalents thereof, and mixtures thereof.

In certain embodiments, a composition comprises L-serine, non-limiting examples of which include free L-serine, and polymers or polypeptides comprising at least a 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% L-serine by weight or amino acid content. In some embodiments, a polymer of L-serine or a polypeptide comprising L-serine includes between 2 and 50,000, between 2 and 500, between 2 and 100, between 2 and 50, between 2 and 20, between 2 and 15, between 2 and 10, between 2 and 9, between 2 and 8, between 2 and 7, between 2 and 6, between 2 and 5, or between 2 and 4 L-serine amino acids linked by covalent bonds. In certain embodiments, a composition comprises L-serine, non-limiting examples of which include a polymer or polypeptide comprising from 20% to 100%, from 30% to 100%, from 35% to 100%, from 40% to 100%, from 45% to 100%, from 50% to 100%, from 55% to 100%, from 60% to 100%, from 65% to 100%, from 70% to 100%, from 75% to 100%, from 80% to 100%, from 85% to 100%, from 90% to 100%, from 95% to 100%, from 96% to 100%, from 97% to 100%, from 98% to 100%, or from 99% to 100% content of L-serine (wt/wt) or amino acid content (i.e., L-serine monomers/total amino acid monomers).

Non-limiting examples of a salt of L-serine include a sodium salt, potassium salt, calcium salt, magnesium salt, zinc salt, ammonium salt; inorganic salts such as hydrogen chloride, sodium chloride, potassium chloride, calcium chloride, sodium phosphate, potassium phosphate, and sodium hydrogen carbonate; organic salts such as sodium citrate, citrate, acetate, and the like. In certain embodiments, a composition comprises L-serine as an alkylated L-serine, such as L-serine with an alkyl group, or e.g., an alkyl comprising 1-20 carbon atoms. In certain embodiments, a derivative of L-serine includes an L-serine ester, an L-serine di-ester, a phosphate ester of L-serine, or a sulfate or sulfonate ester of L-serine. Non-limiting examples of a conjugate of L-serine includes a pegylated L-serine (e.g., an L-serine comprising one or more polyethylene glycol (PEG) moieties), and a lipidated L-serine. Non-limiting example of a precursor of L-serine include L-phosphoserine.

Non-limiting examples of a precursor of L-serine include a pro-form of L-serine that is broken down into L-serine monomers by the digestive system of a subject. In some embodiments, L-serine or a conjugate thereof consists of a slow-release version. In some embodiments, a derivative of L-serine is conjugated to a different molecule forming a prodrug from which L-serine is released after crossing the blood/brain barrier.

In some embodiments, a composition consisting essentially of L-serine may comprise some amount of D-serine. For example, a composition consisting essentially of L-serine may include a small amount of D-serine, for example, less than 30%, less than 25%, less than 20%, less than 15%, less than 10%, less than 9%, less than 8%, less than 7%, less than 6%, less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, or less than 0.1% D-serine by weight (e.g., wt/wt) or amino acid content (e.g., D-serine/total amino acid content). For example, a composition may include from 0.001% to 30%, from 0.005% to 30%, from 0.1% to 30%, from 1% to 30%, from 2% to 30%, from 3% to 30%, from 4% to 30%, from 5% to 30%, from 6% to 30%, from 7% to 30%, from 8% to 30%, from 9% to 30%, from 10% to 30%, from 0.001% to 20%, from 0.005% to 20%, from 0.1% to 20%, from 1% to 20%, from 2% to 20%, from 3% to 20%, from 4% to 20%, from 5% to 20%, from 6% to 20%, from 7% to 20%, from 8% to 20%, from 9% to 20%, or from 10% to 20% D-serine. In some embodiments, a composition comprising or consisting essentially of L-serine, does not comprise a substantial amount of D-serine. In some embodiments, a composition comprising or consisting essentially of L-serine, does not contain D-serine.

Any suitable method can be used to detect and/or quantitate the presence, absence and/or amount of 2-aminoethyl dihydrogen phosphate and/or taurine in a sample. In certain embodiments, the presence, absence and/or amount of 2-aminoethyl dihydrogen phosphate and/or taurine in a sample is determined by a method comprising the use of mass spectrometry (MS).

As used herein, an "amount" refers to a mass, weight, volume, and/or a concentration of a substance in a sample. An amount may be an average, mean, maximum, or absolute amount. A maximum amount may be an average, mean or absolute maximum amount. In certain embodiments, an amount is a ratio of an amount of a first substance (e.g., 2-aminoethyl dihydrogen phosphate) in a sample to an amount of a second substance (e.g., taurine) in a sample (e.g., the same sample).

In some embodiments, an amount is compared to a predetermined threshold amount. In some embodiments, an amount is determined to be below, substantially the same as, or above a predetermined threshold amount. In some embodiments, a predetermined threshold amount is an amount of a substance in a sample obtained from a healthy subject. In some embodiments, a predetermined threshold amount is an amount of a substance determined in one or more samples obtained from one or more healthy subjects. In some embodiments, a predetermined threshold amount is an amount of 2-aminoethyl dihydrogen phosphate determined in one or more samples obtained from one or more healthy subjects. In some embodiments, a predetermined threshold amount is an amount of taurine determined in one or more samples obtained from one or more healthy subjects. In some embodiments, a predetermined threshold amount is a ratio of 2-aminoethyl dihydrogen phosphate to taurine determined in one or more samples obtained from one or more healthy subjects.

In certain embodiments, a predetermined threshold amount of taurine in blood plasma is an amount equal to or less than 200 moles/L (taurine/vol plasma), equal to or less than 175 moles/L, equal to or less than 150 moles/L, equal to or less than 140 moles/L, equal to or less than 130 moles/L, or equal to or less than 125 moles/L. In certain embodiments, a predetermined threshold amount of 2-aminoethyl dihydrogen phosphate in blood plasma is an amount equal to or less than 100 moles/L (2-aminoethyl dihydrogen phosphate/vol plasma), equal to or less than 90 moles/L, equal to or less than 80 moles/L, equal to or less than 75 moles/L, equal to or less than 70 moles/L, or equal to or less than 60 moles/L.

In some embodiments, a predetermined threshold amount that is a ratio of 2-aminoethyl dihydrogen phosphate to taurine is an average, mean or absolute ratio of 0.30 or less, 0.25 or less, 0.20 or less, 0.19 or less, 0.18 or less, 0.17 or less, 0.16 or less, 0.15 or less, or 0.14 or less.

In certain embodiments, an amount of 2-aminoethyl dihydrogen phosphate and/or taurine in a sample obtained from a subject that indicates that a subject has, or is at risk of developing AD, is an amount that is about 20-fold, about 19-fold, about 18-fold, about 17-fold, about 16-fold, about 15-fold, about 14-fold, about 13 fold, about 12 fold, about 11 fold, about 10.5 fold, about 10 fold, about 9.5 fold, about 9 fold, about 8.5 fold, about 8 fold, about 7.5 fold, about 7 fold, about 6.5 fold, about 6 fold, about 5.5 fold, about 5 fold, about 4.5 fold, about 4 fold, about 3.5 fold, about 3 fold, about 2.9 fold, about 2.8 fold, about 2.7 fold, about 2.6 fold, about 2.5 fold, about 2.4 fold, about 2.3 fold, about 2.2 fold, about 2 fold, about 1.9 fold, about 1.8 fold, about 1.7 fold, about 1.6 fold, about 1.5 fold, about 1.4 fold, about 1.3 fold, about 1.2, or about 1.1 fold higher than the predetermined threshold amount.

In certain embodiments, a ratio of 2-aminoethyl dihydrogen phosphate to taurine in a sample obtained from a subject that indicates that a subject has, or is at risk of developing AD, is a ratio of 2-aminoethyl dihydrogen phosphate to taurine that is about 20-fold, about 19-fold, about 18-fold, about 17-fold, about 16-fold, about 15-fold, about 14-fold, about 13 fold, about 12 fold, about 11 fold, about 10.5 fold, about 10 fold, about 9.5 fold, about 9 fold, about 8.5 fold, about 8 fold, about 7.5 fold, about 7 fold, about 6.5 fold, about 6 fold, about 5.5 fold, about 5 fold, about 4.5 fold, about 4 fold, about 3.5 fold, about 3 fold, about 2.9 fold, about 2.8 fold, about 2.7 fold, about 2.6 fold, about 2.5 fold, about 2.4 fold, about 2.3 fold, about 2.2 fold, about 2 fold, about 1.9 fold, about 1.8 fold, about 1.7 fold, about 1.6 fold, about 1.5 fold, about 1.4 fold, about 1.3 fold, about 1.2, or about 1.1 fold higher than the predetermined threshold amount (ratio) of 2-aminoethyl dihydrogen phosphate to taurine.

In some embodiments, methods provided herein can be performed two or more times thereby monitoring the progression of Alzheimer's disease in a subject and/or monitoring a response to treatment of Alzheimer's disease in a subject.

Administration

Any suitable method of administering a treatment or drug to a subject can be used. Any suitable formulation and/or route of administration can be used for administration of a treatment or drug disclosed herein (e.g., see Fingl et al. 1975, in "The Pharmacological Basis of Therapeutics", which is incorporated herein by reference in its entirety). A suitable formulation and/or route of administration can be chosen by a medical professional (e.g., a physician) in view of, for example, a subject's disease, condition, symptoms, weight, age, and/or general health. Non-limiting examples of routes of administration include topical or local (e.g., transdermally or cutaneously (e.g., on the skin or epidermis), in or on the eye, intranasally, transmucosally, in the ear, inside the ear (e.g., behind the ear drum)), enteral (e.g., delivered through the gastrointestinal tract, e.g., orally (e.g., as a tablet, capsule, granule, liquid, emulsion, lozenge, or combination thereof), sublingual, by gastric feeding tube, rectally, and the like), by parenteral administration (e.g., parenterally, e.g., intravenously, intra-arterially, intramuscularly, intraperitoneally, intradermally, subcutaneously, intracavity, intracranial, intra-articular, into a joint space, intracardiac (into the heart), intracavernous injection, intralesional (into a skin lesion), intraosseous infusion (into the bone marrow), intrathecal (into the spinal canal), intrauterine, intravaginal, intravesical infusion, intravitreal), and the like or combinations thereof.

In some embodiments, administering a drug to a subject comprises providing the drug to the subject, for example for self-administration or for administration to the subject by another (e.g., by a non-medical professional). As another example, a drug can be provided as an instruction written by a medical practitioner that authorizes a patient to be provided a drug or treatment described herein (e.g., a prescription). In yet another example, a drug can be provided to a subject wherein the subject self-administers a composition orally, intravenously or by way of an inhaler, for example.

Alternately, one can administer a drug in a local rather than systemic manner, for example, via direct application to the skin, mucous membrane or region of interest for treating, including using a depot or sustained release formulation.

In certain embodiments a drug is administered alone (e.g., as a single active ingredient (AI) or, e.g., as a single active pharmaceutical ingredient (API)). In other embodiments, a drug is administered in combination with one or more additional AIs/APIs, for example, as two separate compositions or as a single composition where the one or more additional AIs/APIs are mixed or formulated together with a drug in a pharmaceutical composition.

In some embodiments, an amount of Alzheimer's disease drug administered to a subject is a therapeutically effective amount. In some embodiments, a therapeutically effective amount of a drug is an amount needed to obtain an effective therapeutic outcome. In certain embodiments, a therapeutically effective amount of a drug is an amount sufficient to treat, reduce the severity of, inhibit or delay the onset of, mitigate and/or alleviate one or more symptoms of Alzheimer's disease. Determination of a therapeutically effective amount is well within the capability of those skilled in the art, especially in light of the detailed disclosure provided herein.

In certain embodiments, a therapeutically effective amount is an amount high enough to provide an effective therapeutic effect (e.g., a beneficial therapeutic effect) and an amount low enough to minimize unwanted adverse reactions. Accordingly, in certain embodiments, a therapeutically effective amount of a drug may vary from subject to subject, often depending on age, weight, general health or condition of a subject, severity of a condition being treated and/or a particular combination of drugs administered to a subject. Thus, in some embodiments, a therapeutically effective amount is determined empirically. Accordingly, in certain embodiments, a therapeutically effective amount of a drug that is administered to a subject can be determined by one of ordinary skill in the art based on amounts found effective in animal or clinical studies, a physician's experience, and/or suggested dose ranges or dosing guidelines.

In certain embodiments, a therapeutically effective amount of L-serine or a composition disclosed herein comprises one or more doses (administered to a subject) comprising at least 0.1 mg/kg, at least 5 mg/kg, at least 10 mg/kg, at least 15 mg/kg, at least 20 mg/kg, at least 25 mg/kg, at least 50 mg/kg, at least 100 mg/kg, at least 250 mg/kg, at least 500 mg/kg, at least 1000 mg/kg, at least 5000 mg/kg, or at least 7500 mg/kg of L-serine, or a salt, a precursor, derivative or conjugate thereof, per kg body weight of a subject.

In some embodiments, administering a therapeutically effective amount of an Alzheimer's disease drug or composition disclosed herein comprises administering a suitable dose hourly, every two hours, every 4 hours, every 6 hours, every 8 hours, or every 12 hours. In certain embodiments, an Alzheimer's disease drug can be administered at least one, at least two, at least three, at least four, at least five, or at least six times per day, e.g., 1 to 12 times per day, 1 to 8 times per day, or 1 to 4 times per day. In certain embodiments, an Alzheimer's disease drug disclosed herein can be administered once, twice, 3 times, 4 times, 5 times, 6 times, 7 times, 8 times, 9 times, 10 times, 11 times, or 12 times per day. An Alzheimer's disease drug may be administered in a single dosage form or in one or more dosage forms. A daily dose can be achieved in the form of a single dose or in the form of a plurality of partial doses.

An Alzheimer's disease drug can be administered on a daily basis or on a schedule containing days where dosing does not take place. For example, dosing may take place every other day, or dosing may take place for 2, 3, 4, or 5 consecutive days of a week, then be followed by from 1 to 5 non-dosing days.

An Alzheimer's disease drug can be administered for at least a day, at least two days, at least three days, at least four days, at least five days, at least a week, at least two weeks, at least three weeks, at least a month, at least two months, at least three months, at least six months, at least a year, at least two years, or more, or for any extended duration to further improve, maintain, or retain therapeutic efficacy. In certain embodiments, an Alzheimer's disease drug is administered for a duration of 1 week to 10 years or more. In some embodiments, administering a therapeutically effective amount of a drug, or a pharmaceutical composition comprising a drug, comprises administering a suitable dose at a frequency or interval as needed to obtain an effective therapeutic outcome. In some embodiments, administering a therapeutically effective amount of a drug or a pharmaceutical composition disclosed herein comprises administering a suitable dose hourly, every two hours, every 4 hours, every 6 hours, three times a day, twice a day, once a day, six times a week, five times a week, four times a week, three times a week, twice a week, weekly, at combinations thereof, and/or at regular or irregular intervals thereof, and/or simply at a frequency or interval as needed or recommended by a medical professional. In some embodiments, a therapeutically effective amount of a drug or a pharmaceutical composition comprising a therapeutically effective amount of drug is administered continuously, for example by intravenous administration.

EXAMPLES

Example 1

Methods

Blood plasma used in this study came from initial blood draws sourced from an FDA-approved, Phase IIa human clinical trial for early-stage Alzheimer's patients (NCT03062449) and from two batches of control samples collected by Innovative Research Inc. (Novi, Michigan, USA). Independent samples were separated into two cohorts using different individuals in each group. The first cohort comprised n=11 early-stage Alzheimer's patients and n=11 controls. The second cohort included n=14 different Alzheimer's patients and n=14 controls also using different individuals.

Blood plasma was collected in K2-EDTA tubes and inverted several times after collection. The sample was centrifuged immediately at 2000×g for 15 minutes at 4° C. Time between blood collection and freezing was less than 1 hour and the sample was stored at –80° C. The plasma sample was thawed in the refrigerator (4° C.) for two hours and combined with an equal volume of cold 10% (w/v) trichloroacetic acid (TCA). The sample was left to precipitate at room temperature for two hours followed by centrifugation at 14,000×g for 5 min. The supernatant was removed by pipette and filtered using a centrifuge filter (0.2 µm PVDF, Millipore Ultrafree®-MC) at 14,000×g for 5 min.

The underivatized supernatant (20 µL) was injected into a Hitachi Amino Acid Analyzer L8900 equipped with a Hitachi Reaction column (PN 855-3533) at 135° C., a high-speed physiological fluid analysis analytical column Li-form resin #26225C 6 mm ID×40 L 060928C (PN855-4515), and Ammonia Filter column (Ion exchange 4.6×40 Column #2650L, PN 855-3523). Hitachi pre-made buffers were used as follows: (B1) PF-1/ANO-5031, (B2) PF-2/ANO-5032, (B3) PF-3/ANO-5033, (B4) PF-4/ANO-5034, (B6) PF-5/ANO-5035, (R1) ninhydrin solution, and (R2) ninhydrin-buffer of lithium acetate dihydrate. Wash solutions included (B5) 5% ethanol, (R3) 10% methanol, and (C1) 10% methanol. Separation was achieved with a flow rate for pump 1 of 0.54 mL/min and 0.47 mL/min for pump 2, reactor column set to 135° C., and a 146 min gradient elution: 0.00 min=100% B1, column oven temp 35° C., 50% R1, 50% R2; 16.0 min=100% B1; 16.1 min=81% B1, 19% B2, column oven 58° C.; 41.0 min=column oven 32° C.; 57.0 min=column oven 70° C.; 69.5 min=column oven 65° C.; 70.0 min=15% B1, 75% B2, 10% B3; 88.0 min=column oven 60° C.; 94.0 min=20% B2, 80% B4; 94.1 min=25% B2, 75% B4; 109.0 min=25% B2, 75% B4, column oven 70° C.; 109.1 min=100% B4; 123.0 min=100% B4; 123.1 min=100% B6; 127.0 min=50% R1, 50% R2; 127.1 min=100% R3; 129.0 min=100% B6, 129.1 min=100% B1; 131.0 min=column oven 35° C.; 132.0 min=100% R3; 132.1 min=50% R1, 50% R2; 146.0 min=100% B1. Amino acid standards (Sigma A6407–acidic amino acids and neutral amino acids+Sigma A6282–basic amino acids) were mixed to equal concentrations and complete standard curves run at concentrations 5, 10, 25, 50 100, 250, 500, 1000 µmon. All amino acids curves were linear within this range ($R^2$=99%). In addition, retention time checks were conducted for 2-aminoethyl dihydrogen phosphate (Sigma-Aldrich P0503-1G) and taurine (Sigma-Aldrich T0625-10G). A lower end curve (1.4, 3.5, 7.1, 14.2, 70.9 µmon) demonstrated that 2-aminoethyl dihydrogen phosphate was linear to 1.4 µmon ($R^2$=99.9%)

Confirmation of 2-aminoethyl dihydrogen phosphate in the samples was conducted through triple quadrupole mass spectrometry. Plasma samples from AD patients and controls were deproteinated as above and derivatized with 6-aminoquinolyl-N-hydroxysuccinimidyl carbamate (AQC, WAT052880, Waters Corp, Milford, MA) using 10 µl of supernatant, 70 µl of borate buffer and 20 µl of AQC. AD blood samples were combined together to obtain a single sample as were control samples and analyzed on a Thermo TSQ Quantiva™ triple quadrupole mass spectrometer with multiple injections per sample. The mass spectrometer was equipped with a Thermo Vanquish™ pump, autosampler, H-ESI probe, and heated column compartment set to 65° C. A Thermo Scientific OPTON-10005 Genius 3022 dual N2 generator (Peak Scientific, Billerica, MA) supplied purified nitrogen to the mass spectrometer. Separation was achieved using a Kinetex C-18 column (1.7 µm 100 A, 100×2.1 mm, 00D-4475-AN); and gradient elution (flow rate 0.5 ml/min, mobile phase A=20 mM ammonium acetate (Fisher Scientific A11450)≥99% adjusted to pH 5.0 with glacial acetic acid (Fisher Scientific A385-500), B=100% methanol≥99.9% Chromasolv; 34885-4×4, Honeywell Burdick & Jackson, Muskegon, MI): initial conditions 99.8% A, 1.0 min 99.8% A, 1.5 min 40% A, 2.0 min 25% A, 2.5 min 25% A, 2.6 min 10% A, 5.5 min 10% A, 6 min 98% A, 8 min 98% A all set with curve 5. The mass spectrometer was run in positive mode (4400 V) with the following settings: spray voltage=static; sheath gas=5.6 Arb; aux gas=23.5 Arb; sweep gas=1.2 Arb; ion transfer tube=150° C.; vaporization temperature=450° C.; Q1 resolution=0.7 FWHM; Q3 resolution=0.7 FWHM; and CID gas=2 mTorr. Scans for derivatized 2-aminoethyl dihydrogen phosphate were conducted with the following transitions (312 to 171.2 m/z collision energy (CE) 17.1, 312 to 142 m/z CE 17.1, 312 to 312 m/z CE 2, RF lens of 90). This experiment was repeated a second time to ensure reproducibility. The limit of detection for this method was 0.004 µg/ml and the lower limit of quantification was 0.01 µg/ml. A standard curve was prepared with concentrations 20 pg/ml, 40 pg/ml, 0.2 ng/ml, 0.4 ng/ml, 2 ng/ml, 4 ng/ml, 10 ng/ml, 20 ng/ml, 0.1 µg/ml, 0.2 µg/ml, linearity had an $R^2$ value of 99%.

Results and Discussion

2-Aminoethyl dihydrogen phosphate consists of a phosphate group linked to the second carbon of ethanolamine and has a molecular weight of 141.06 g/mol. It can be biosynthesized from ethanolamine (Human Metabolome Database; HMDB0000224) and is involved in phosphotidylcholine synthesis and is a precursor for phosphotidylethanolamine. It is a solid with a melting point of 242° C.

In the first Hitachi amino acid analyzer experiment, we found 2-aminoethyl dihydrogen phosphate peaks in AD patients (n=11) to be consistently high while 2-aminoethyl dihydrogen phosphate in the controls (n=11), if present, were below our limits of detection. We repeated this experiment with blood plasma from a new cohort of AD patients (n=14) and a new set of control plasma (n=14). In the second experiment, we noticed overly large taurine peaks in eight control plasma samples. Because taurine elutes close to 2-aminoethyl dihydrogen phosphate after separation in the C-18 column early in the chromatography (1.6 and 2.0 min respectively; FIG. 1), the high taurine concentrations in a few samples created a separation issue between these two peaks. This artificially raised the area under the 2-aminoethyl dihydrogen phosphate curve in these samples. To correct for this issue, we calculated a 2-aminoethyl dihydrogen phosphate/taurine ratio in both experiments and identified a highly significant difference (p<0.0001) between the ratios for AD patients and controls using a two-tailed Mann Whitney U test (Table 1).

TABLE 1

| | | | | | |
|---|---|---|---|---|---|
| Ratio of phosphoethanolamine to taurine (2-aminoethyl dihydrogen phosphate/Tau) in blood plasma from early-stage Alzheimer's patients (AD) and controls. The difference between the AD and control ratios was highly significant using a two-tailed Mann Whitney U test. Data were quantified from the Hitachi amino acid analyzer. | | | | | |
| | AD median (range, n) | Control median (range, n) | U-value | z | P-value |
| Experiment 1 | 0.36 (0.21-0.66, 14) | 0.15 (0.00-0.00, 14) | 121 | 3.94 | <0.0001 |
| Experiment 2 | 0.34 (0.24-0.76, 11) | 0.00 (0.00-0.50, 11) | 184 | 3.93 | <0.0001 |

The concentration of taurine in blood plasma of normal individuals is generally thought to be low, ranging from 25 to 150 moles/L (Jacobsen and Smith 1968). Measurements of plasma taurine concentrations in our samples varied widely between individuals in this study (range 3 to 403 moles/L) with 8/50 showing values over 150 moles/L. We attribute the high values in these eight samples to come from contamination of the plasma by platelets or leukocytes which are rich in taurine (Jacobsen and Smith 1968) and note that all of these samples came from a single batch of controls received from Innovative Research Inc. while none of the samples from the Phase II AD trial showed the same pattern of contamination and none of the controls from the first batch received from Innovative Research Inc. had the same problem.

We cannot rule out the possibility that taurine was, for some reason, naturally high in the eight control patients. High taurine concentrations have been shown to result in an increase in extracellular 2-aminoethyl dihydrogen phosphate. In an in vivo rabbit model, the administration of taurine (2 mM) to the dorsal hippocampus resulted in an observed increase in 2-aminoethyl dihydrogen phosphate over time (Lehmann and Hamberger 1984). The study concluded that, together, taurine and 2-aminoethyl dihydrogen phosphate might stabilize synaptosomal membrane calcium fluxes as a reduction in the phospholipid content of these tissues which can result in decreased calcium transport (Lehmann and Hamberger 1984). However, high naturally occurring taurine in blood plasma can be corrected for with a 2-aminoethyl dihydrogen phosphate/taurine ratio.

As a concentration comparison to other studies, we note that only a few studies that report amino acid concentrations in blood plasma report 2-aminoethyl dihydrogen phosphate concentrations. Of those that do, reference ranges for healthy adults extend from "not detected" to up to 69 μmoles/L (Perry and Hansen 1969, McGale et al. 1977, Slocum and Cummings 1991, Tan and Gajra 2006). The Mayo clinic reports reference ranges for amino acids and indicates normal 2-aminoethyl dihydrogen phosphate concentrations as follows: <12 for adults 18 and older, <5 for children ages 2-17 years, and <6 for children under the age of two years old (neurology.testcatalog.org/show/AAQP). Quantification of amino acids is very dependent on the methods employed and variation in method collection, processing, storing, and instrumentation used for detection will create variability. The strength of our study is that all samples were collected using the same protocol and analyzed on the same instrument providing highly comparable data. concentrations. Of those that do, reference ranges for healthy adults extend from "not detected" to up to 69 moles/L (Perry and Hansen 1969, McGale et al. 1977, Slocum and Cummings 1991, Tan and Gajra 2006). The Mayo clinic reports reference ranges for amino acids and indicates normal 2-aminoethyl dihydrogen phosphate concentrations as follows: <12 for adults 18 and older, <5 for children ages 2-17 years, and <6 for children under the age of two years old (URL: https://neurology.testcatalog.org/show/AAQP). Quantification of amino acids is very dependent on the methods employed and variation in method collection, processing, storing, and instrumentation used for detection will create variability. The strength of our study is that all samples were collected using the same protocol and analyzed on the same instrument providing highly comparable data.

The prominent 2-aminoethyl dihydrogen phosphate presence found in AD blood plasma but not appreciably in control samples represents a promising blood biomarker for AD. Since blood draws are routine in clinical practice, it has the potential to be used as a diagnostic indicator, which can be detected using standard amino acid analyzers present in most large hospital and diagnostic laboratories. In addition, the accumulation of 2-aminoethyl dihydrogen phosphate may teach us important aspects about the cellular pathways that go awry in AD.

Confirmation of 2-aminoethyl dihydrogen phosphate was conducted in two experiments by mass spectrometry. 2-Aminoethyl dihydrogen phosphate was present and in 5-10× higher concentrations in the AD samples than in the control plasma samples. The 2-aminoethyl dihydrogen phosphate in the first Hitachi amino acid analyzer analysis were also 10× higher in the AD samples than what was seen in the controls.

Figure 2:
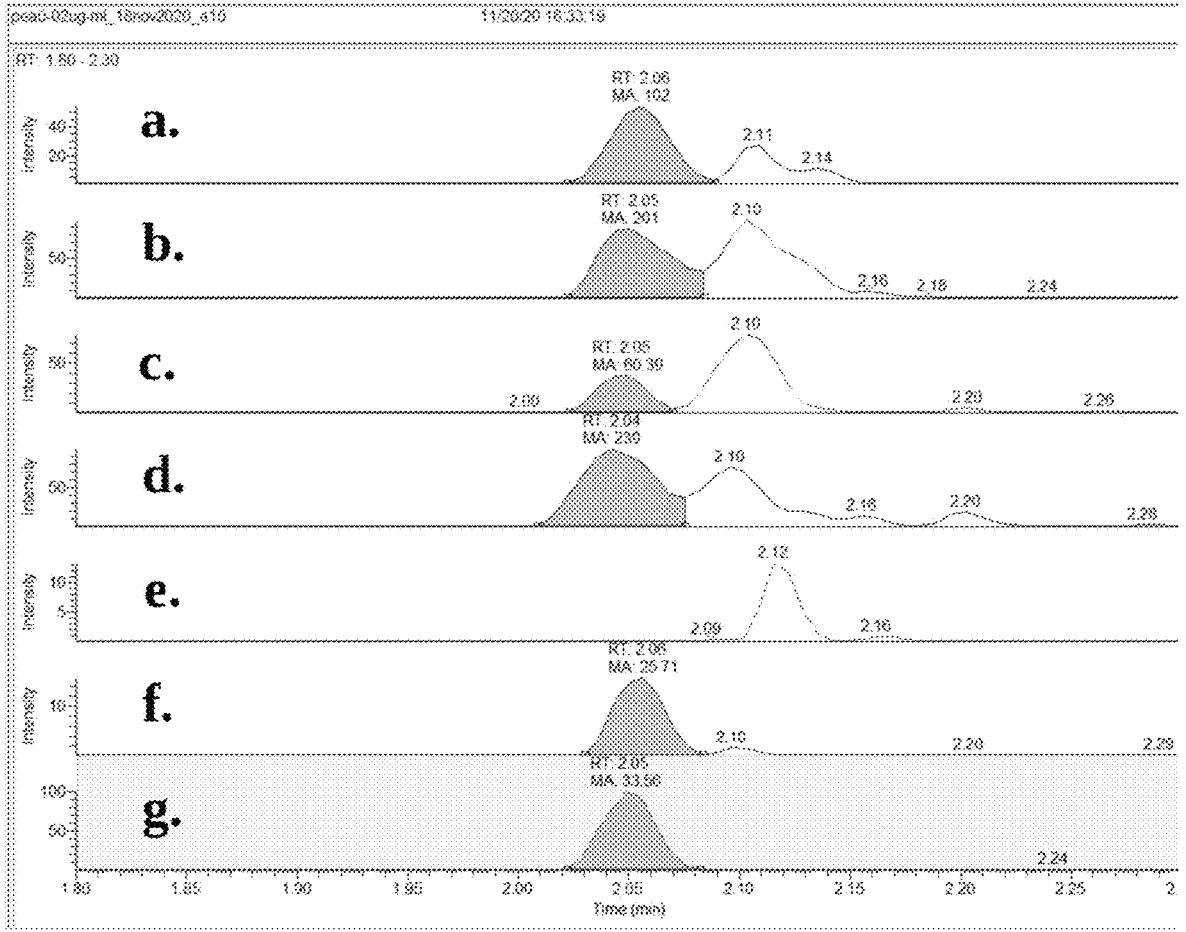
FIG. 2 shows Triple quadrupole mass spectrometer chromatographs of derivatized and combined early stage Alzheimer's disease (AD) samples and controls: (a) AD 3 μl injection volume, experiment 1; (b) AD 6 μl injection, experiment 1; (c) AD 6 μl injection, experiment 2; d) AD 6 μl injection spiked with 0.15 ng 2-aminoethyl dihydrogen phosphate standard, experiment 2; (e) controls 3 μl injection, experiment 1 (2-aminoethyl dihydrogen phosphate not detected); (f) control 6 μl injection, experiment 1; (g) 2-aminoethyl dihydrogen phosphate standard 3 μl injection of 0.004 μg/ml with a peak at 2.05 min retention time.

In the first mass spectrometer experimental analysis the area under the curve from the combined AD samples had ten times the area as the combined control samples with minor variation between injections (mean=208+/−13 stdev for AD and 27+/−13 for controls from n=5 injections; n=11 AD samples; n=10 control samples; FIG. 2 a, b, e, f). In the second replication AD samples had five times the area in comparison with the control samples (mean 55+/−9AD; 10+/−6 controls; n=4 injections; n=11 AD samples; n=11 controls. FIG. 2 c, d). The area was above the limit of quantification (LOQ) for AD samples only in the first experiment (0.1 μg/ml) and all others were below the LOQ but above the limit of detection (LOD).

We note that although the peaks were small in the MS/MS analysis they double in area consistent with injection volume (FIG. 2 a, b) and a low concentration spike increases only the peak at 2.05 min consistent with the retention time of the 2-aminoethyl dihydrogen phosphate standard (FIG. 2 c, d, g). We do not know the identity of the peak at 2.10, which is found only in the plasma samples and not in the 2-aminoethyl dihydrogen phosphate standard (FIG. 2).

2-Aminoethyl dihydrogen phosphate is important in the structure and function of cellular membranes and in mammals is a precursor for phosphatidylethanolamine and phosphatidylcholine. 2-Aminoethyl dihydrogen phosphate is essential for the biosynthesis of mammalian glycosylphosphatidylinositol-anchored proteins (GPI) which bind proteins to the plasma membrane and is evolutionarily highly conserved (Kamitani et al., 1992). The biological activity of the GPI is not fully known, but may play a role in cellular communication, cellular signaling, signal transduction, and in lipid raft transports (Paulick et al., 2008). Research suggests that the proximate source of the 2-aminoethyl dihydrogen phosphate in GPI synthesis is phosphatidyletha-nolamine (Menon et al., 1993).

In cell culture, 2-aminoethyl dihydrogen phosphate has been shown to inhibit mitochondrial respiration and induce apoptosis by disrupting the mitochondrial membrane potential (Modica-Napolitano and Renshaw 2004, Ferreira et al., 2013). The effect of increased 2-aminoethyl dihydrogen phosphate concentrations in the blood is entirely unknown. Of interest is the reverse observation that the concentration of 2-aminoethyl dihydrogen phosphate in the brain is lower in AD patients than in controls (Ellison et al. 1987). In that study, 2-aminoethyl dihydrogen phosphate concentrations were significantly lower in the temporal cortex (64%, Brodmann area 21), frontal cortex (48%, Brodmann area 9), and hippocampus (40%) but not in the parietal (Brodmann area 3-12) or occipital cortices (Brodmann area 17) of postmortem AD brain tissue. In Huntington's disease, 2-aminoethyl dihydrogen phosphate was lower in both the CSF and in postmortem brain tissue when compared to control tissues. Significant differences were found in the caudate, putamen, and nucleus accumbens but not the frontal cortex (Ellison et al. 1987, Koroshetz et al., 1997). Similarly, a significant decrease in 2-aminoethyl dihydrogen phosphate has also been noted in the putamen of Parkinson's disease (PD) patients in comparison to control brain tissue according to proton magnetic resonance spectroscopy imagining studies (Hattingen et al., 2009). Hattingen et al., 2009 suggests that this reflects reduced membrane turnover as a result of impaired mitochondrial function. Mitochondrial dysfunction has been considered as a contributing factor to AD by some researchers (Sheng et al., 2012). The importance of 2-aminoethyl dihydrogen phosphate as a substrate in the synthesis of cellular membranes and its increased concentration in the blood, but not in the brain of AD patients, suggests that further study of this molecule might lead to new insights in the study of neurodegeneration.

One pathway of interest that intersects with a Phase IIa clinical trial on early-stage Alzheimer's disease, testing if L-serine can slow the progression of AD (NCT03580616), is the de novo sphingolipid biosynthesis pathway where serine palmitoyltransferase catalyzes the reaction of L-serine with palmitoyl-Coenzyme A to form sphingoid bases. It is intriguing that the breakdown of both sphinganine and sphingosine leads to the production of 2-aminoethyl dihydrogen phosphate (Duan and Merrill 2015; Harrison et al., 2018). Furthermore, in vitro, an increase in sphinganine kinase has been shown to decrease the concentration of free sphinganine which resulted in the disruption of axonal growth in cultured hippocampal neurons (van Echten-Deckert 1998). Sphingolipid metabolism is thought to be tightly regulated as the metabolites play a role in cellular signal transduction (van Echten-Deckert 1998). If the sphingolipid biosynthesis pathway was disrupted in AD, an increase in the downstream 2-aminoethyl dihydrogen phosphate could result. In addition, a need for additional L-serine to drive the pathway forward could also occur (Metcalf et al., 2018). Furthermore, it has been suggested that altered phospholipid composition of plasma membranes can result in abnormal signal transduction and membrane breakdown can also contribute to neurodegeneration in AD (Wells et al., 1995; Gonzalez-Dominguez et al., 2014). Research predictive of an increase in 2-aminoethyl dihydrogen phosphate in this pathway, as shown empirically in our study, might lead to new insights into AD etiology.

In a rare inherited disease known as hypophosphatasia individuals have elevated 2-aminoethyl dihydrogen phosphate, primarily in urine (Goyer 1963, Imbard 2012, Whyte 2016, Salles 2020). The disease is thought to be caused by mutations in the tissue-nonspecific alkaline phosphatase (TNSALP) gene (Salles 2020). The symptoms of this disease are highly variable but always include problems with bone and teeth mineralization and frequently includes neurological complications (Linglart and Biosse-Duplan 2016).

REFERENCES

BAYRAM, et al., "Current understanding of magnetic resonance imaging biomarkers and memory in Alzheimer's disease", Alzheimer's & Dementia Translational Research & Clinical Interventions, 2018, doi: 10.1016/j.trci.2018.04.007.

CUMMINGS, et al., "Alzheimer's drug-development pipeline: few candidates, frequent failures", AD Research & Therapy", August 2014, pp. 1-7, Vol. 6 (4).

ELLISON, et al., "Phosphoethanolamine and ethanolamine are decreased in Alzheimer's disease and Huntington's disease", Brain Research, 11 Aug. 1987, pp. 389-392, Vol. 417 (2).

FERREIRA, et al., "Synthetic 2-aminoethyl dihydrogen phosphate induces cell cycle arrest and apoptosis in human breast cancer MCF-7 cells through the mitochondrial pathway", Biomedicine & Pharmacotherapy, 1 Jul. 2013, pp. 481-487, Vol. 67 (6).

GONZALEZ-DOMINGUEZ, et al., "Metabolomic study of lipids in serum for biomarker discovery in Alzheimer's disease using direct infusion mass spectrometry", Journal of Pharmaceutical and Biomedical Analysis, 2014, doi: 10.1016/j.jpba.2014.05.023.

GOYER, R A, "Ethanolamine phosphate excretion in a family with hypophosphatasia", Archives of Disease in Childhood, June 1963, pg. 205, Vol. 38 (199).

HARRISON, et al., "Sphingolipid biosynthesis in man and microbes", Nat Prod Rep., 19 Sep. 2018, pp. 921-954, Vol. 35 (9). doi: 10.1039/c8np00019k. PMID: 29863195; PMCID: PMC6148460.

HATTINGEN, et al., "Phosphorus and proton magnetic resonance spectroscopy demonstrates mitochondrial dysfunction in early and advanced Parkinson's disease", Brain, December 2009, pp. 3285-3297, Vol 132 (12), doi: 10.1093/brain/awp293.

IMBARD, et al., "2-aminoethyl dihydrogen phosphate normal range in pediatric urines for hypophosphatasia screening", Clinical Chemistry and Laboratory Medicine, 1 Dec. 2012, pp. 2231-2233, Vol. 50 (12).

JACK J R., "Hypothetical model of dynamic biomarkers of the Alzheimer's pathological cascade", The Lancet Neurology, 1 Jan. 2010, pp. 119-128, Vol. 9 (1).

JACOBSEN, et al., "Biochemistry and physiology of taurine and taurine derivatives", Physiological Reviews, April 1968, pp. 424-511, Vol. 48 (2).

KAMITANI, et al., "Complexity of ethanolamine phosphate addition in the biosynthesis of glycosylphosphatidylinositol anchors in mammalian cells", Journal of Biological Chemistry, December 1992, pp. 24611-24619, Vol. 267 (34).

KONDO, et al., "Identification of the phytosphingosine metabolic pathway leading to odd-numbered fatty acids", Nature Communications, 27 Oct. 2014, pp. 1-11, Vol. 5:5338.

KOROSHETZ, et al., "Energy metabolism defects in Huntington's disease and effects of coenzyme Q10", Annals of Neurology: Official Journal of the American Neurological Association and the Child Neurology Society, February 1997, pp. 160-165, Vol. 41 (2).

KUMAR, et al., "The sphingolipid degradation product trans-2-hexadecenal induces cytoskeletal reorganization and apoptosis in a JNK-dependent manner", Cellular Signalling, July 2011, pp. 1144-1152, Vol. 23 (7) 2011.

LAWRENCE, et al., "A Systematic Review of Longitudinal Studies Which Measure Alzheimer's Disease Biomarkers", Journal of Alzheimer's Disease, 2017, pp. 1359-1379, Vol. 59 (4), doi: 10.3233/jad-170261.

LEHMANN, et al., "A possible interrelationship between extracellular taurine and 2-aminoethyl dihydrogen phosphate in the hippocampus", Journal of Neurochemistry, May 1984, pp. 1286-1290, Vol. 42 (5).

LINGLART, et al., "Hypophosphatasia", Current Osteoporosis Reports, 2016, pp. 95-105, Vol. 14 (3).

LOVELL, et al., "Use of bomb pulse carbon-14 to age senile plaques and neurofibrillary tangles in Alzheimer's disease", Neurobiology of Aging, 2002, pp. 179-186, Vol. 23 (2).

MCCONATHY, et al., "Imaging Biomarkers Associated with Cognitive Decline: A Review", Biological Psychiatry", 15 Apr. 2015, pp. 658-692, Vol. 77 (8), doi: 10.1016/j.biopsych.2014.08.024.

MEHTA, et al, "Why do trials for Alzheimer's drugs keep failing? A discontinued drug perspective for 2010-2015:, Expert Opinion on Investigational Drugs, June 2017, pp. 735-739, Vol. 26 (6).

MENON, et al.," Phosphatidylethanolamine is the donor of the terminal 2-aminoethyl dihydrogen phosphate group in trypanosome glycosylphosphatidylinositols", The EMBO Journal 1993, doi: 10.1002/j.1460-2075.1993.tb05839.x.

METCALF, et al., "L-Serine: a naturally-occurring amino acid with therapeutic potential", Neurotoxicity Research", January 2018, pp. 213-221, Vol. 33 (1).

MODICA-NAPOLITANO, et al., "Ethanolamine and 2-aminoethyl dihydrogen phosphate inhibit mitochondrial function in vitro: implications for mitochondrial dysfunction hypothesis in depression and bipolar disorder", Biological Psychiatry, February 2004, pp. 273-277, Vol. 55 (3).

MULLANE, et al, "Alzheimer's Disease (AD) therapeutics-1: Repeated clinical failures continue to question the amyloid hypothesis of AD and the current understanding of AD causality", Biochemical Pharmacology, December 2018, pp. 359-375, 1; 158.

PAULICK, et al., "The glycosylphosphatidylinositol anchor: a complex membrane-anchoring structure for proteins", Biochemistry, July 2008, pp. 6991-7000, Vol. 47 (27).

OLSSON et al., "CSF and blood biomarkers for the diagnosis of Alzheimer's disease: a systematic review and meta-analysis", The Lancet Neurology, 1 Jun. 2016, pp. 673-684, Vol. 15 (7).

SALLES, J P, "Hypophosphatasia: Biological and Clinical Aspects, Avenues for Therapy", The Clinical Biochemist Reviews, February 2020, pg. 13, Vol. 41 (1).

SCHINDLER, et al., "High-precision plasma β-amyloid 42/40 predicts current and future brain amyloidosis", Neurology, 2019, pp. e1647-e1659, Vol. 93, available at: www.ncbi.nlm.nih.gov/pubmed/31371569.

SHENG, et al., "Impaired mitochondrial biogenesis contributes to mitochondrial dysfunction in Alzheimer's disease", Journal of Neurochemistry, 2012, doi: 10.1111/j.1471-4159.2011.07581.x.

VAN ECHTEN-DECKERT, et al., "1-Methylthiodihydroceramide, a Novel Analog of Dihydroceramide, Stimulates Sphinganine Degradation Resulting in Decreased de Novo Sphingolipid Biosynthesis", Journal of Biological Chemistry, 1998, doi: 10.1074/jbc.273.2.1184.

WELLS, et al., "Neural membrane phospholipids in Alzheimer disease", Neurochemical Research, 01November 1995, pp. 1329-1333, Vol. 20 (11).

WHYTE, M., "Hypophosphatasia-aetiology, nosology, pathogenesis, diagnosis and treatment", Nat Rev Endocrinol, 2016, pp. 233-246, https://doi.org/10.1038/nrendo.2016.14.

The entirety of each patent, patent application, publication or any other reference or document cited herein hereby is incorporated by reference. In case of conflict, the specification, including definitions, will control.

Citation of any patent, patent application, publication or any other document is not an admission that any of the foregoing is pertinent prior art, nor does it constitute any admission as to the contents or date of these publications or documents.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All of the features disclosed herein may be combined in any combination. Each feature disclosed in the specification may be replaced by an alternative feature serving a same, equivalent, or similar purpose. Thus, unless expressly stated otherwise, disclosed features (e.g., antibodies) are an example of a genus of equivalent or similar features.

As used herein, all numerical values or numerical ranges include integers within such ranges and fractions of the values or the integers within ranges unless the context clearly indicates otherwise. Further, when a listing of values is described herein (e.g., about 50%, 60%, 70%, 80%, 85% or 86%) the listing includes all intermediate and fractional values thereof (e.g., 54%, 85.4%). Thus, to illustrate, reference to 80% or more, includes 81%, 82%, 83%, 84%, 85%, 86%, 87%, 88%, 89%, 90%, 91%, 92%, 93%, 94%, etc., as well as 81.1%, 81.2%, 81.3%, 81.4%, 81.5%, etc., 82.1%, 82.2%, 82.3%, 82.4%, 82.5%, etc., and so forth.

Reference to an integer with more (greater) or less than includes any number greater or less than the reference number, respectively. Thus, for example, a reference to less than 100, includes 99, 98, 97, etc. all the way down to the number one (1); and less than 10, includes 9, 8, 7, etc. all the way down to the number one (1).

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth.

Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-1,000, 1,000-1,500, 1,500-2,000, 2,000-2,500, 2,500-3,000, 3,000-3,500, 3,500-4,000, 4,000-4,500, 4,500-5,000, 5,500-6,000, 6,000-7,000, 7,000-8,000, or 8,000-9,000, includes ranges of 10-50, 50-100, 100-1,000, 1,000-3,000, 2,000-4,000, etc.

Modifications can be made to the foregoing without departing from the basic aspects of the technology. Although the technology has been described in substantial detail with reference to one or more specific embodiments, those of ordinary skill in the art will recognize that changes can be made to the embodiments specifically disclosed in this application, yet these modifications and improvements are within the scope and spirit of the technology.

The invention is generally disclosed herein using affirmative language to describe the numerous embodiments and aspects. The invention also specifically includes embodiments in which particular subject matter is excluded, in full or in part, such as substances or materials, method steps and conditions, protocols, or procedures. For example, in certain embodiments or aspects of the invention, materials and/or method steps are excluded. Thus, even though the invention is generally not expressed herein in terms of what the invention does not include aspects that are not expressly excluded in the invention are nevertheless disclosed herein.

The technology illustratively described herein suitably can be practiced in the absence of any element(s) not specifically disclosed herein. Thus, for example, in each instance herein any of the terms "comprising," "consisting essentially of," and "consisting of" can be replaced with either of the other two terms. Some embodiments of the technology described herein suitably can be practiced in the absence of an element not specifically disclosed herein. Accordingly, in some embodiments the term "comprising" or "comprises" can be replaced with "consisting essentially of" or "consisting of" or grammatical variations thereof. A composition "consisting essentially of" refers to a composition that includes only the active ingredients claimed (e.g., active ingredient (AI) or active pharmaceutical ingredient (API); e.g., L-serine, a salt, metabolic precursor, derivative or conjugate thereof); which composition may include other ingredients such as formulation materials, excipients, additives, carriers, preservatives, diluents, solvents, fillers, salts, buffers, coatings, binders, and lubricating agents; and which composition excludes other APIs not claimed.

The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. The term, "substantially" as used herein refers to a value modifier meaning "at least 95%", "at least 96%", "at least 97%", "at least 98%", or "at least 99%" and may include 100%. For example, a composition that is substantially free of X, may include less than 5%, less than 4%, less than 3%, less than 2%, or less than 1% of X, and/or X may be absent or undetectable in the composition.

Thus, it should be understood that although the present technology has been specifically disclosed by representative embodiments and optional features, modification and variation of the concepts herein disclosed can be resorted to by those skilled in the art, and such modifications and variations are considered within the scope of this technology.

What is claimed is:

1. A method of identifying and treating a subject who has, or is suspected of having Alzheimer's disease comprising:
   (a) determining an amount of 2-aminoethyl dihydrogen phosphate in a sample obtained from the subject,
   (b) determining that if the subject has, or is suspected of having Alzheimer's disease according to the amount of the 2-aminoethyl dihydrogen phosphate in the sample, and
   (c) administering a therapeutically effective amount of an Alzheimer's disease drug to the subject, wherein the Alzheimer's disease drug is selected from the group consisting of ralitoline, phenytoin, lamotrigine, carbamazepine, lidocaine, tetrodotoxin, nitroindazole, a sulforaphane or sulforaphane analogue, gabapentin, pregabalin, mirogabalin, gabapentin enacarbil, phenibut, imagabalin, atagabalin, 4-methylpregabalin, PD-217,014, riluzole, edaravone, tetrabenazine, haloperidol, risperidone, quetiapine, amantadine, levetiracetam, clonazepam, citalopram, escitalopram, fluoxetine, sertraline, olanzapine, valproate, carbamazepine, lamotrigine, a vaccine, a cholinesterase inhibitor, memantine, an antidepressant, an N-methyl D-aspartate (NMDA) antagonist, an omega-3 fatty acid, curcumin or a curcumin derivative, vitamin E, a sleep aid, an anti-anxiety drug, an anti-convulsant, an anti-psychotic, carbidopa-levodopa, amantadine, a dopamine agonists, a Monoamine Oxidase Type B (MAO-B) inhibitor, a Catechol O-methyltransferase (COMT) inhibitor, and an anticholinergic.

2. The method of claim 1, wherein (a) further comprises determining an amount of taurine, and (b) comprises determining that the subject has, or is suspected of having Alzheimer's disease according to the amount of the 2-aminoethyl dihydrogen phosphate and taurine in the sample.

3. The method of claim 1, wherein the subject is determined in (b) to have or to be at risk of developing Alzheimer's disease when the amount of 2-aminoethyl dihydrogen phosphate is above a predetermined threshold amount.

4. The method of claim 3, wherein the amount of 2-aminoethyl dihydrogen phosphate above the predetermined threshold amount is an amount that is selected from the group consisting of about 20-fold, about 19-fold, about 18-fold, about 17-fold, about 16-fold, about 15-fold, about 14-fold, about 13 fold, about 12 fold, about 11 fold, about 10.5 fold, about 10 fold, about 9.5 fold, about 9 fold, about 8.5 fold, about 8 fold, about 7.5 fold, about 7 fold, about 6.5 fold, about 6 fold, about 5.5 fold, about 5 fold, about 4.5 fold, about 4 fold, about 3.5 fold, about 3 fold, about 2.9 fold, about 2.8 fold, about 2.7 fold, about 2.6 fold, about 2.5 fold, about 2.4 fold, about 2.3 fold, about 2.2 fold, about 2 fold, about 1.9 fold, about 1.8 fold, about 1.7 fold, about 1.6 fold, about 1.5 fold, about 1.4 fold, about 1.3 fold, about 1.2, and about 1.1 fold higher than the predetermined threshold amount.

5. The method of claim 3, wherein the predetermined threshold amount is an average, mean, absolute or maximum amount of 2-aminoethyl dihydrogen phosphate that is present in one or more healthy control subjects.

6. The method of claim 3, wherein the determining of the amount in (a) comprises determining a ratio of 2-aminoethyl dihydrogen phosphate to taurine, and the determining of (b) comprises determining that the subject has, or is suspected of having Alzheimer's disease according to the ratio of 2-aminoethyl dihydrogen phosphate to taurine in the sample.

7. The method of claim 6, wherein the subject is determined in (b) to have or to be suspected of having Alzheimer's disease when the ratio of 2-aminoethyl dihydrogen phosphate to taurine is above a predetermined threshold amount.

8. The method of claim 7, wherein the ratio of 2-aminoethyl dihydrogen phosphate to taurine that is above the predetermined threshold amount is a ratio that is selected from the group consisting of about 20-fold, about 19-fold, about 18-fold, about 17-fold, about 16-fold, about 15-fold, about 14-fold, about 13 fold, about 12 fold, about 11 fold, about 10.5 fold, about 10 fold, about 9.5 fold, about 9 fold, about 8.5 fold, about 8 fold, about 7.5 fold, about 7 fold, about 6.5 fold, about 6 fold, about 5.5 fold, about 5 fold, about 4.5 fold, about 4 fold, about 3.5 fold, about 3 fold, about 2.9 fold, about 2.8 fold, about 2.7 fold, about 2.6 fold, about 2.5 fold, about 2.4 fold, about 2.3 fold, about 2.2 fold, about 2 fold, about 1.9 fold, about 1.8 fold, about 1.7 fold, about 1.6 fold, about 1.5 fold, about 1.4 fold, about 1.3 fold, about 1.2, and about 1.1 fold higher than the predetermined threshold amount.

9. The method of claim 7, wherein the predetermined threshold amount is an average, mean, absolute or maximum amount of a ratio of 2-aminoethyl dihydrogen phosphate to taurine present in one or more healthy control subjects.

10. The method of claim 1, wherein the Alzheimer's disease drug is selected from ralitoline, phenytoin, lamotrigine, carbamazepine, lidocaine, tetrodotoxin, riluzole, edaravone, gabapentin, pregabalin, mirogabalin, gabapentin enacarbil, phenibut, imagabalin, atagabalin, 4-methylpregabalin, PD-217,014, trihexyphenidyl, amitriptyline, baclofen, diazepam and CK-2127107.

11. The method of claim 1, wherein the sample comprises blood or a blood product.

12. The method of claim 11, wherein the blood product comprises or consists of plasma.

13. The method of claim 1, wherein the subject is a mammal.

14. The method of claim 13, wherein the mammal is a non-human primate.

15. The method of claim 14, wherein the non-human primate is a vervet.

16. The method of claim 1, wherein the subject is a human.

17. The method of claim 1, wherein the subject is asymptomatic for Alzheimer's disease.

18. The method of claim 1, further comprising monitoring the progression of Alzheimer's disease in the subject, wherein the method is conducted two or more times.

19. The method of claim 1, wherein the subject is not diagnosed with Alzheimer's disease prior to the determining of (b).

20. The method of claim 1, wherein the method is an ex vivo method.

21. The method of claim 1, wherein the method is an in vitro method.

* * * * *